United States Patent [19]

Choudhury et al.

[11] Patent Number: 5,220,053

[45] Date of Patent: Jun. 15, 1993

[54] PREPARATION OF OPTICALLY ACTIVE ALIPHATIC CARBOXYLIC ACIDS

[75] Inventors: Azfar A. Choudhury; Abbas Kadkhodayan; Deepak R. Patil, all of Orangeburg, S.C.

[73] Assignee: Ethyl Corporation, Richmond, Va.

[21] Appl. No.: 825,055

[22] Filed: Jan. 24, 1992

[51] Int. Cl.$^5$ ............................................. C07B 57/00
[52] U.S. Cl. ................................... 562/401; 548/572; 549/499; 549/79; 560/10; 560/15; 560/100; 560/102; 560/105; 560/152; 560/248
[58] Field of Search ......................... 562/401; 548/572; 549/599; 560/248, 10, 15, 100, 102, 105, 152

[56] References Cited

U.S. PATENT DOCUMENTS

| | | | |
|---|---|---|---|
| 4,724,102 | 2/1988 | Cannata et al. | 562/401 |
| 4,752,417 | 6/1988 | Inoue et al. | 562/401 |
| 4,973,745 | 11/1990 | Blaschke et al. | 562/401 |

Primary Examiner—José G. Dees
Assistant Examiner—Vera C. Clarke
Attorney, Agent, or Firm—Richard J. Hammond

[57] ABSTRACT

An improved process for the separation of enantiomers of a racemic mixture of certain aliphatic carboxylic acids or esters thereof is disclosed. The process involves adding a mixture of the aliphatic carboxylic acid to the material formed by: (i) forming a solution comprising said racemic mixture of a $C_1$ to $C_6$ linear or branched aliphatic carboxylic acid and an organic or inorganic solvent; (ii) treating said solution with a chiral organic nitrogenous base; (iii) precipitating from the reaction solution formed in step (ii) a crystalline material comprised of the less soluble diastereomeric salt. The solution is admixed with the crystalline material for a time sufficient to cause an increase in the amount of the less soluble diastereomeric salt in the crystalline material.

13 Claims, No Drawings

PREPARATION OF OPTICALLY ACTIVE ALIPHATIC CARBOXYLIC ACIDS

FIELD OF THE INVENTION

This invention relates to an improvement in a process for the preparation of optically active carboxylic acids and the esters thereof. More particularly this invention relates to an improved process for the preparation of aliphatic carboxylic acids and the esters thereof by adding to a mixture of the diastereomeric salts of such materials a solution of the aliphatic carboxylic acid or ester thereof for a time sufficient to cause the crystalline material to increase in the concentration of one of the salts and then separating the diastereomeric salt.

BACKGROUND OF THE INVENTION

Resolution of racemic aryl-substituted aliphatic carboxylic acids has been described in the literature. Kaiser et al., *J. Pharm. Sci.*, Vol. 65, No. 2, 269-273 (February 1976) formed the $S(-)$-$\alpha$-methylbenzylamine salt of $S(+)$-ibuprofen, removed it from the reaction mixture by filtration, and recrystallized it from isopropanol and then from methanol. After acidifying the 3N aqueous sulfuric acid and extracting with ether, $S(+)$-ibuprofen was obtained, m.p. 50.14 52., $[\alpha]_D + 57$., with 95% optical purity as determined by GLC analysis. Cox et al., *J. Pharmacol. Exp. Ther.*, Vol. 232, No. 3, 636-643 (March 1985), using the Kaiser et al. method. were able to obtain an $S(+)$-ibuprofen preparation which was 99% S isomer and 1% R isomer (w/w).

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is less soluble. The (+)-salt can then be acid cleaved to yield pure enantiomer. See, for example, U.S. Pat. No. 4,209,638 issued Jun. 24, 1980, and U.S. Pat. No. 3,637,767 issued Jan. 25, 1972, which relate to resolution of naproxen and related compounds.

U.S. Pat. No. 5,015,764 discloses and claims a process for increasing the amount of the desired enantiomer obtained from a racemic mixture of $C_1$ to $C_6$ linear or branched aliphatic carboxylic acid or ester thereof. The process comprises: (i) forming a mixture comprising the racemic mixture of the $C_1$ to $C_6$ linear or branched aliphatic carboxylic acid or ester thereof and an organic or inorganic solvent; (ii) treating said salt solution with a chiral organic nitrogenous base; (iii) precipitating from the reaction solution produced in the treatment of step (ii) a crystalline material that is comprised of greater than 50% of one diastereomeric salt; and (iv) separating said diastereomeric salt. The disclosure of this patent is incorporated herein by reference.

According to the process of the present invention, an improvement of the above process has been discovered. Reaction steps (i), (ii) and (iii) are carried out as disclosed. At this point in the reaction sequence, a two-phase mixture is produced that is essentially the solid diastereomeric salt and the remaining reaction liquid. The solid is dispersed in near emulsion form throughout the liquid. It is typically separated by filtration leaving the mother liquor filtrate and solid filtered residue. The residue requires numerous recrystallizations before a product of satisfactory purity is obtained. This process of successive crystallization significantly reduces the amount of final product recovery of satisfactory purity. The conventional separation processes are inconvenient and time consuming, disadvantageously producing multiple process streams and reducing yield of the product significantly.

It has now been discovered that an improved crystalline product can be obtained, at significantly higher yields, from the crystalline material of step iii) by adding to such crystalline material a solution of the same $C_1$ to $C_6$ linear or branched aliphatic carboxylic acid or ester thereof. It should be understood that the term "racemic mixture" as used throughout this specification is intended to include enantiomer mixtures of 1:1, S to R ratio, through to mixtures of 99% of one of said enantiomers (an enantiomerically enriched racemic mixture).

While not wishing to be bound by the following, it is known that the crystalline material precipitated from the treatment step ii) is a mixture of enantiomeric salts of the carboxylic acids (or esters thereof), the mixture being of greater than 50% concentration in one of the salts. The precipitated mixture has a high concentration of the less soluble enantiomer in the solvent used to form the salt solution of step i). The more soluble enantiomer remains in solution. As such, the slurry formed from step iii) is an equilibrium mixture of the enantiomeric salts. Addition of a solution of the racemic mixture of the aliphatic carboxylic acid upsets this equilibrium by first interacting with the more soluble diastereomeric salt causing the newly formed, less soluble enantiomer to precipitate. This interaction/precipitation continues until a new equilibrium is established. However, the end result is that the amount of less soluble enantiomer in the crystalline material is increased. As such, the process of the present invention is a purification or optical enrichment process with significantly higher recoveries in yield.

Preferably, under these reaction conditions, the solvent used for dissolving the racemic mixture of the aliphatic carboxylic acid or ester thereof is a $C_5$ to $C_{12}$ linear or branched hydrocarbon optionally substituted with one or more halo groups or it is an aromatic hydrocarbon optionally substituted with one or more $C_1$ to $C_6$ linear or branched alkyl, nitriles, amides, halo or hydroxyl group. Most preferably, the solvent is selected from the group consisting essentially of hexanes, heptanes, octane, benzene, toluene, xylenes, methanol, ethanol, propanols, butanols, pentanols, hexanols, linear or branched amides, diamides and substituted amides or mixtures thereof.

The $C_1$ to $C_6$ linear or branched aliphatic carboxylic acids and esters useful in the improved process of the present invention have the formula

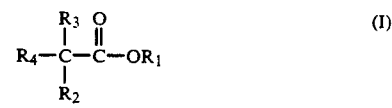

where $R_1$ is hydrogen or $C_1$ to $C_6$ linear or branched alkyl or substituted linear or branched alkyl; $R_2$, $R_3$ and $R_4$ are independently the same or different and are hydrogen or $C_1$ to $C_6$ linear or branched alkyl, e.g., methyl or ethyl; aralkyl, e.g., benzyl; cycloalkyl, e.g., cyclopropyl, cyclobutyl, cyclopentyl, cyclohexyl; alkyl substituted cycloalkyl, e.g., methylcyclohexyl; $C_6$ to $C_{10}$ aryl, e.g., phenyl unsubstituted or substituted with, for example, methyl, dimethyl, butyl especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., phenoxy or phenoxy substituted with, for example, methyl dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl; $C_1$ to $C_4$ alkoxy, e.g., ethoxy, halo; or biphenyl unsubstituted or substituted with methyl or halo, especially fluoro.

Preferred compounds of formula I are those of the formula

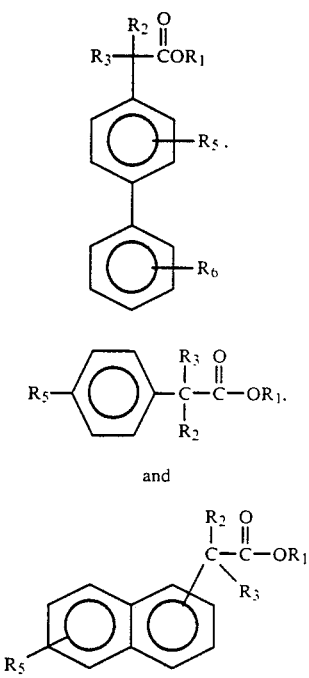

and wherein $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The improved process is particularly applicable to 2-(4-isobutylphenyl)propionic acid and especially in obtaining a preponderance of the S(−) isomer.

The process is carried out by using a racemic mixture [a mixture of both the (+) and (−) or dextro and levo rotatory forms] or a mixture containing a preponderance of one of the enantiomers of these carboxylic acids. The use of a 1:1 racemic mixture is preferred. Because the separation of isomers gives rise to a soluble product largely containing one enantiomer and an insoluble product largely containing the other enantiomer, a high purity salt is obtained that requires a minimum number of recrystallizations (usually not more than one) to give a product with exceptional high optical purity at significantly higher yields.

The purified enantiomeric salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even greater extent.

The first step in the reaction sequence for the separation of the racemic mixtures used in the present invention is to form a mixture of the aliphatic carboxylic acid with a solvent. The solvent employed to form the mixture is preferably a liquid and inert. Most preferably, but not limited to, such solvents include the aliphatic hydrocarbon solvents, i.e., $C_4$ to $C_{14}$ hydrocarbons, $C_1$ to $C_6$ alcohols, nitriles, amides, and halides. Particularly preferred are hexanes, heptanes, octanes and water as such solvent.

The chiral organic nitrogenous base is next added. It forms a more stable salt with the isomers of the aliphatic carboxylic acid. Further, one of the diastereomeric salts formed from the chiral organic nitrogenous base is more soluble in the reaction solution (the solution formed when the chiral base is added to the salt solution), the other, of course, precipitates. The solid crystalline precipitate is readily separated from the solution by conventional techniques, i.e., centrifugation, filtration and the like. It is this material that is used as the starting material for the purification process of the present invention.

It should be noted that the process of the present invention is particularly adapted to the economical conversion of racemic mixtures to the diastereomeric S- or R- component. The method of the present invention essentially provides a solid precipitate enriched in the S-enantiomer and a liquid filtrate enriched in the R-enantiomer. Liberation of the desired S-enantiomer from the precipitated salt is readily accomplished by acidification of the salt with, for example, dilute mineral acid or any other inorganic or organic acid conventionally known to hydrolyze salts of this nature. This procedure leaves the R-enriched filtrate as a by-product. If the desired product is the R-isomer, the filtrate can be treated in a conventional manner to recover the R-isomer. The filtrate, as such, can be racemized via conventional methods and recycled. This mixture can then be reused in the process of the present invention, using the chiral organic base recovered from the above conversion step. Thus, the process of the present invention lends itself readily to a recycling-type of procedure.

EXAMPLES

The invention is illustrated by the following Examples.

EXAMPLE 1

To a 3-liter flask equipped with an agitator, thermometer, reflux condenser and an addition funnel, were charged 206 grams (1 mole) of racemic ibuprofen and 1,700 mL of hexane. The contents of the reactor were heated to 50° C. and 60.5 grams (0.5 mole) of S-methylbenzyl amine were fed over 2 hours. The reaction mass was filtered to isolate the solids, washed with hexane, and dried (161.5 grams). The solids were then added to 1,000 grams of 1M sulfuric acid and the resultant mass extracted with 3 portions each of 500 mL hexane. The extracts were combined and analyzed for % S-enantiomer (75% or 50% ee). The extracts were evaporated to isolate 101.5 grams ibuprofen enriched in S-enantiomer (98.5% yield based on S-methylbenzyl amine).

EXAMPLE 2

Using part of the procedure of Example 1, the salt of ibuprofen and S-methylbenzyl amine (161.5 grams, 75% S-enantiomer) was prepared. This was dissolved in 475 mL of methanol at 75° C. Upon cooling to −10° C., the precipitated solids were filtered, washed with cold methanol, dried and analyzed. 111.4 grams, 90% S-enantiomer). These solids represent a 69% yield based on S-methylbenzyl amine.

EXAMPLE 3

Two further crystallizations using the procedure outlined in Example 2 were required to achieve the S-enantiomer content in the salt greater than 99%. 54.1 grams of the salt thus recovered represent 33.1% yield.

EXAMPLE 4

Using part of the procedure outlined in Example 1, 161.5 grams of ibuprofen and S-methylbenzyl amine salt were prepared (75% S-enantiomer). These solids were slurried in 1,700 mL of hexane and to this mixture were added 102 grams of racemic ibuprofen. The contents were heated to 68° C. and agitated for 4 hours and then cooled to 25° C. and filtered. The solids were washed with hexane, dried (155 grams) and analyzed (91% S-enantiomer). The yield was 96%.

EXAMPLE 5

Using part of the procedure outlined in Example 4, 161.5 grams of ibuprofen and S-methylbenzyl amine salt were prepared (75% S-enantiomer) These solids were slurried in 1,700 mL of hexane and to this mixture were added 102 grams 75% S-enantiomeric ibuprofen. The contents were heated to 68° C. and agitated for 4 hours and then cooled to 25° C. and filtered. The solids were washed with hexane, dried (155 grams) and analyzed (95% S-enantiomer). The yield was 96%.

EXAMPLE 6

The procedure of Example 4 was repeated with the following variations: 300 mL of methanol were used as solvent and the final slurry was cooled to −10° C. The filtered solids were dried (139.5 grams) and analyzed (92% S-enantiomer). The yield was 86%.

EXAMPLE 7

The procedure of Example 4 was repeated with the following variations: 50 mL of triethylamine and 450 mL of water were used as solvent and the final slurry was cooled to 20° C. The filtered solids were dried (154 grams) and analyzed (91% S-enantiomer). The yield was 95.3%.

EXAMPLE 8

The filtrate from Example 4 was concentrated to 1,000 mL. 100 mL of 1N HCl were used to wash the concentrate. The concentrate was washed twice with 50 mL portions of water. The hexane layer was evaporated to dryness to recover 105.5 grams of ibuprofen (37% S-enantiomer).

EXAMPLE 9

The filtrate from Example 4 was concentrated to 1,000 mL to which 100 mL of triethylamine were added. The whole was heated to 140° C. under pressure for 4 hours. Upon cooling, the reaction mass was washed with 1,000 mL of 1N HCl followed by two 100 mL portions of water. The hexane layer was evaporated to dryness and 104 grams of racemic ibuprofen were recovered.

We claim:

1. In a process for separating the enantiomers of a racemic mixture of a $C_1$ to $C_6$ linear or branched aliphatic carboxylic acid or ester thereof, by a process comprising: (i) forming a mixture of said carboxylic acid and a solvent; (ii) treating said mixture with a chiral organic nitrogenous base; (iii) precipitating from the reaction solution formed in step (ii) a crystalline material that is comprised of greater than 50% of the salt of one enantiomer of said $C_1$ to $C_6$ linear or branched aliphatic carboxylic acid or ester thereof; the improvement comprising treating said crystalline material with a mixture of said racemic mixture of a $C_1$ to $C_6$ linear or branched aliphatic carboxylic acid or ester thereof for a time sufficient to cause an increase in the amount of said salt of one enantiomer in said crystalline material; and separating the crystalline material increased with one enantiomer salt.

2. The process according to claim 1 wherein solvent for said solution is an aliphatic or aromatic hydrocarbon optionally substituted with one or more alkyl, halo, nitro, cyano, carboxylic acid or ester thereof, hydroxy, thio, thioether group or water.

3. The process according to claim 2 wherein the solvent is a $C_5$ to $C_{12}$ linear or branched hydrocarbon optionally substituted with one or more halo groups or an aromatic hydrocarbon optionally substituted with alkyl or halo.

4. The process according to claim 3 wherein the solvent is selected from the group consisting of hexane, heptane, octane, benzene, toluene, xylene, water and mixtures thereof.

5. In a process for separating the diastereomers from a racemic mixture of 2-(4-isobutylphenyl)propionic acid which process comprises: (i) forming a solution comprising said racemic mixture and a solvent; (ii) treating said solution at a temperature of about 25° C. to about 125° C. with a chiral organic base that is $C_1$ to $C_6$ linear or branched aliphatic amine or a $C_1$ to $C_6$ linear or branched aliphatic amine further substituted with $C_6$ to $C_{10}$ aryl group that is unsubstituted or substituted with $C_1$ to $C_6$ alkyl, $C_1$ to $C_6$ alkoxy or halo, or $C_1$ to $C_6$ linear or branched alkoxy; (iii) precipitating from the reaction solution formed in step (ii) a crystalline material comprised of the less soluble diastereomeric salt; the improvement comprising treating the precipitated less soluble diastereomeric salt with a solution of said racemic mixture of 2-(4-isobutylphenyl)propionic acid for a time sufficient to cause an increase in the amount of said less soluble diastereomeric salt in said crystalline material and separating the crystalline material increased with said diastereomeric salt.

6. The process according to claim 5 wherein the solvent for said solution of the mixture of 2-(4-isobutylphenyl)propionic acid is an aliphatic or aromatic hydrocarbon optionally substituted with one or more alkyl, halo, nitro, cyano, carboxylic acid or ester thereof, hydroxy, thio, thioether group.

7. The process according to claim 6 wherein the solvent is a $C_5$ to $C_{12}$ linear or branched hydrocarbon optionally substituted with one or more halo groups or an aromatic hydrocarbon optionally substituted with alkyl or halo.

8. The process according to claim 7 wherein the solvent is selected from the group consisting of hexane, heptane, octane, benzene, toluene, xylene, water and mixtures thereof.

9. The process of claim 5 wherein said separated salt is hydrolyzed and the free optically active 2-(4-isobutylphenyl)propionic acid and the chiral amine are recovered.

10. The process of claim 9 wherein said optically active 2-(4 isobutylphenyl)propionic acid has S(+) configuration.

11. The process of claim 5 wherein a residual solution is obtained after separation of the precipitated salt containing the more soluble salt of R-enantiomer and said residual solution is treated to racemize the R-enantiomer into the salt of racemic (R,S) mixture for recycling.

12. The process of claim 5 wherein a residual solution is obtained after separation of the precipitated salt containing the more soluble R-enantiomer and said residual solution is treated to recover the R-enantiomer.

13. The process of claim 9 wherein said optically active 2-(4-isobutylphenyl)propionic acid has the R(−) configuration.

* * * * *